| United States Patent [19] | [11] | Patent Number: | 4,952,709 |
|---|---|---|---|
| Ohkuma et al. | [45] | Date of Patent: | Aug. 28, 1990 |

[54] ANTITUMOR ANTIBIOTIC BU-3285T COMPOUNDS

[75] Inventors: Hiroaki Ohkuma; Koji Tomita, both of Tokyo; Masataka Konishi, Kawasaki; Hideo Kamei, Tokyo, all of Japan

[73] Assignee: Bristol Myers Company, New York, N.Y.

[21] Appl. No.: 431,423

[22] Filed: Nov. 3, 1989

Related U.S. Application Data

[63] Continuation-in-part of Ser. No. 378,677, Jul. 12, 1989, abandoned.

[51] Int. Cl.$^5$ ............................................. C07D 309/32
[52] U.S. Cl. ..................................................... 549/292
[58] Field of Search ......................................... 549/292

[56] References Cited

U.S. PATENT DOCUMENTS

| 4,495,286 | 1/1985 | Tunc et al. | 435/253 |
| 4,578,383 | 3/1986 | Stampwala et al. | 549/222 |
| 4,680,416 | 7/1987 | Hokanson et al. | 549/292 |

OTHER PUBLICATIONS

*The Merck Index*, Windholz et al., 10th Edition, 1983, p. 2215, Entry No. 2216.

*Primary Examiner*—Mary C. Lee
*Assistant Examiner*—Zinna Northington-Davis
*Attorney, Agent, or Firm*—David M. Morse

[57] ABSTRACT

The present invention relates to the antitumor antibiotic compound BU-3285T and its preparation. The compound is obtained by culturing a new strain of *Chainia rosea* and demonstrates both antitumor and antifungal activity. It also relates to the desulfated derivative of BU-3285T which is obtained by treatment of BU-3285T with sulfatase enzyme. BU-3285T desulfate possesses antitumor activity.

2 Claims, 2 Drawing Sheets

… … …

ANTITUMOR ANTIBIOTIC BU-3285T COMPOUNDS

CROSS-REFERENCE TO RELATED APPLICATIONS

This application is a continuation-in-part of our co-pending application Ser. No. 378,677 filed July 12, 1989, now abandoned.

BACKGROUND OF THE INVENTION

1. Field of the Invention

The present invention relates to a novel antitumor antibiotic, BU-3285T, and a process for preparing same by culturing microorganisms belonging to the genus Chainia. This compound demonstrates a high level of antitumor activity and also possesses antifungal activity. The invention also relates to BU-3285T desulfate which is obtained by enzymatic cleavage of the sulfate linkage of BU-3285T with certain sulfatase enzymes. The desulfated derivative possesses antitumor activity.

2. Description of the Prior Art

Amongst the prior art references of which the applicants are aware, the following represent what is believed to be the closest prior art.

U.S. Pat. No. 4,495,286 which issued on Jan. 22, 1985, discloses a biologically pure culture of the microorganisms Streptomyces-pulveracus subspecies fostreus ATCC 31906, which is capable of producing the CL 1565 antibiotic complex, which is useful as an antibiotic and antitumor agent(s).

U.S. Pat. No. 4,578,383 which issued on Mar. 25, 1986, teaches novel phosphorous containing antibiotic compounds, CL 1565, and their salts, as well as pharmaceutical compositions containing various salts of the compounds alone or in combination with other antitumor agents.

U.S. Pat. No. 4,680,416, which issued July 14, 1987 teaches novel pyranone compounds and related compounds, methods of preparing the compounds and their use as cytotoxic and/or antileukemic agents.

None of these references teaches the novel compounds of the present invention or their use as antitumor and antifungal antibiotic agents.

SUMMARY OF THE INVENTION

Figure 1:
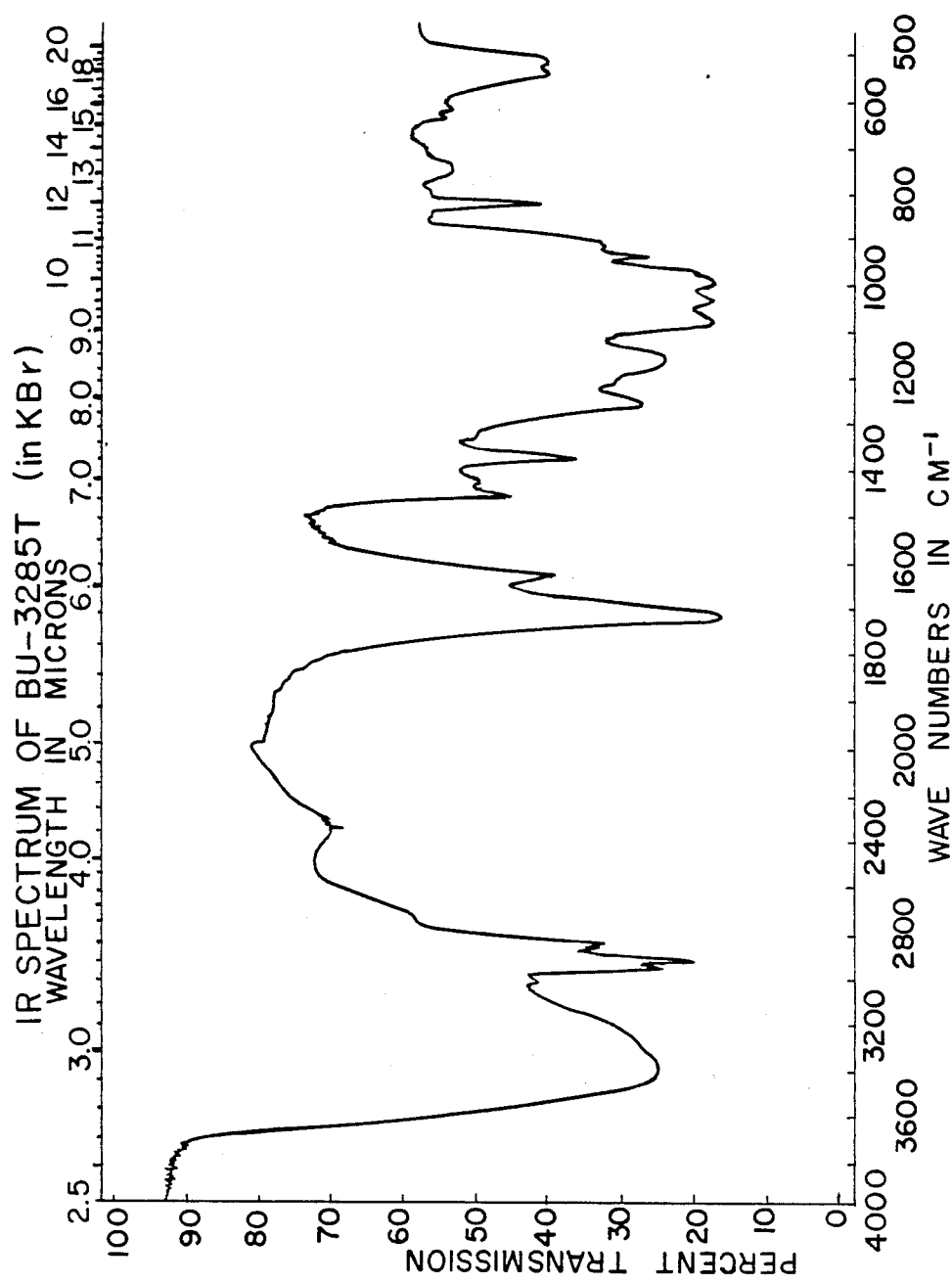
FIG. 1 shows the IR spectrum of BU-3285T.

This invention relates to a novel antitumor and antifungal antibiotic designated BU-3285T and to a fermentation process for production of BU-3285T using a new actinomycete designated herein as Chainia rosea strain L827-7 (ATCC-53903). The invention also relates to the desulfated derivative of BU-3285T and to its production by enzymatic treatment of BU-3285T with certain sulfatases. BU-3285T desulfate has been found to possess antitumor activity.

DETAILED DESCRIPTION OF THE INVENTION

The preferred producing strain for production of BU-3285T is an actinomycete, Strain No. L827-7, which was isolated from a soil sample collected in Gujarat State in India. A mixture of the new antibiotic BU-3285T along with the known co-produced substances, chromomycin, pentalenolactone and aburamycin, was obtained by fermentation of this strain.

Based upon the morphology, cultural and physiological characteristics and cell chemistry, the above-mentioned producing strain was identified as a species of Chainia, i.e., Chainia rosea.

Morphology: The aerial mycelium is not formed or is scantily produced on agar media. Substrate mycelia are well-branched and non-fragmentary. In the substrate mycelium, a balloon-like, semi-transparent body (3–10 $\mu$m) with single or plural phorous hyphae is predominantly born, which becomes a sclerotic, globular body (10–60 $\mu$m in diameter). Scanning electron microscopy shows the globular surface is waved and has no membrane. Ultrathin section micrographs indicate the globules envelop irregularly coiled and partially swollen hyphae which are cemented with an extracellular metabolite.

The aerial mycelium, scarcely formed, bears compact or open-spiral spore chains (20–50 or more spores per chain). The spores are oval or oblong (0.6×0.8–1.2 $\mu$m), and have a smooth surface.

Cultural and physioloqical characteristics: Aerial mycelium are usually not formed, but are seen scantily on ISP media Nos. 4 and 7. The reverse color of substrate mycelium is deep orange to dark reddish-brown. These pigments are not diffusible.

Melanin is not produced and tyrosinase reaction is negative.

Cell chemistry: Whole cell hydrolysate contains LL-diaminopimelic acid and mannose, and hence belongs to Type I. The phospholipids contain phosphatidylethanolamine, and thus are placed in Pattern P-II. The globule bodies contain 2,3-diaminopropionic acid.

Variants: Spontaneous variants which form well aerial mycelium occur upon repeated transfers.

Taxonomic position: The globular bodies are identified as a sclerotium which is described in Chainia.[1,2] The morphology and cell chemistry revealed that Strain L827-7 is classified into the genus Chainia. The cultural and physiological characteristics shown in Tables 1 and 2, clarified that the strain is similar to Chainia aurea, C. flava, C. minutisclerotica, C. rosea, and C. rubra, especially to C. rosea among 15 species of the genus.[1,2,3] Thus, Strain L827-7 was identified as a new strain of Chainia rosea.

[1]Lechevalier, M. P.; H. A. Lechevalier and C. E. Heintz: Morphological and chemical nature of the Sclerotia of Chainia olivacea Thirumalachar and sukapure of the order Actinomycetales. Int. J. Syst. Bacteriol. 23: 157–170, 1973.
[2]Ruan, J.; M. P. Lechevalier, C. Jiang and H. A. Lechevalier: Chainia kunmingensis, a new actinomycete species found in soil. Int. J. Syst. Bacteriol. 35: 164–168, 1985.
[3]Shirling, E. B. and D. Gottlieb: Cooperative description of type strain of Streptomyces. V. Additional descriptions. Int. J. Syst. Bacteriol. 22: 265–394, 1972.

TABLE 1

| | Cultural Characteristics of Strain L827-7 | | | |
|---|---|---|---|---|
| Medium | Growth | Aerial mycelium | Reverse color | Diffusible pigment |
| Sucrose-nitrate agar (Czapek-Dox agar) | Good | None | Moderate reddish-brown (43) | None |

TABLE 1-continued

Cultural Characteristics of Strain L827-7

| Medium | Growth | Aerial mycelium | Reverse color | Diffusible pigment |
| --- | --- | --- | --- | --- |
| Tryptone-yeast extract broth (ISP No. 1) | Moderate, not turbid | None | Colorless | None |
| Yeast extract-malt extract agar (ISP No. 2) | Good | None | Deep orange (51) | Dark orange yellow (72) |
| Oatmeal agar (ISP No. 3) | Moderate | None | Moderate yellow (87) | Grayish yellow (90) |
| Inorganic salts-starch agar (ISP No. 4) | Moderate | Poor; white | Brownish orange (54) | None |
| Glycerol-asparagine agar (ISP No. 55) | Moderate | None | Dark reddish brown (44) | Light reddish brown (42) |
| Peptone-yeast extract-iron agar (No. 6) | Poor | None | Colorless | None |
| Tyrosine agar (ISP No. 7) | Moderate | Scant; white | Dark brown (59) | Moderate brown (58) |
| Glucose-asparagine agar | Poor | None | Strong yellow (84) | None |
| Nutrient agar | Poor | None | Colorless | None |
| Bennett's agar | Moderate | None | Strong yellow (84) | None |

Observation after incubation at 28° C. for 3 weeks.
Color and number in parenthesis follow ISCC-NBS color-name charts.

TABLE 2

Physiological Characteristics of Strain L827-7

| Hydrolysis of: | | | |
| --- | --- | --- | --- |
| | | Lactose | + |
| | | Cellubiose | + |
| Gelatin | + | Melibose | − |
| Starch | + | Trehalose | + |
| Xanthine | − | Raffinose | − |
| | | D-Melezitose | − |
| Milk: | | | |
| Coagulation | + | Soluable starch | + |
| Peptonization | + | Cellulose | − |
| | | Dulcitol | − |
| Tolerance to: | | Inositol | +$^w$ |
| | | D-Mannitol | + |
| Lysozyme 0.01% | − | D-Sorbitol | − |
| 0.001% | + | Salicin | + |
| NaCl 1-7% | + | Benzoate | − |
| 8% | − | Oxalate | + |
| pH 5.0-10.5 | + | Tartrate | − |
| Temperature: | | Acid production from: | |
| Growth range | 18° C.-45° C. | Adonitol | − |
| Optimal growth | 35° C.-40° C. | Dulcitol | − |
| No growth | 14° C. & 48° C. | Erythritol | − |
| | | i-Inositol | +$^w$ |
| Production of: | | Lactose | + |
| | | D-Mannitol | + |
| Nitrate reductase | −/+* | D-Melibiose | + |
| Tyrosinase | − | α-Methylglucoside | +$^w$ |
| Urease | + | Raffinose | − |
| | | L-Rhamnose | + |
| Utilization of: | | D-Sorbitol | − |
| | | Sucrose | − |
| Glyercol | + | D-Xylose | + |
| D-Arabinose | − | | |
| L-Arabinose | + | | |
| D-Xylose | + | | |
| D-Ribose | + | | |
| L-Rhamnose | + | | |
| D-Glucose | + | | |
| D-Galactose | + | | |
| D-Fructose | + | | |
| D-Mannose | + | | |
| L-Sorbose | − | | |
| Sucrose | +$^{w**}$ | | |

*Czapek's sucrose-nitrate broth/Peptone-nitrate broth
**+$^w$, weakly positive

A biologically pure culture of *Chainia rosea* strain no. L827-7 has been deposited with the American Type Culture Collection, Rockville, Maryland, under the accession number ATCC-53903.

As is the case with other microorganisms, the characteristics of the new BU-3285T-producing culture of the present invention, *Chainia rosea* ATCC-53903, are subject to variation. Recombinants, variants and mutants of the ATCC-53903 strain may be obtained by treatment with various known mutagens such as ultraviolet rays, X-rays, high frequency waves, radioactive rays and chemicals. Natural and induced variants, mutants and recombinants of *Chainia rosea* ATCC-53903 which retain the characteristic of producing BU-3285T are intended to be encompassed by the present invention.

BU-3285T may be produced by cultivating a BU-3285T-producing strain of *Chainia rosea*, preferably *Chainia rosea* ATCC-53903 or a mutant or variant thereof, under submerged aerobic conditions in an aqueous nutrient medium. The organism is grown in a nutrient medium containing an assimilable carbon source, for example an assimilable carbohydrate. Examples of suitable carbon sources include lactose, glycerol, sucrose, corn starch, glucose, mannose, fructose, cellobiose, trehalose, mannitol and xylose. The nutrient medium should also contain an assimilable nitrogen source such as, for example, fish meal, peptone, soybean flour, peanut meal, cotton seed meal and corn steep liquor. Nutrient inorganic salts may also be incorporated in the medium and such salts may comprise any of the usual salts capable of providing sodium, potassium, ammonium, calcium, phosphate, sulfate, chloride, bromide, nitrate, carbonate or like ions.

Production of the BU-3285T antibiotic may be effected at any temperature conducive to satisfactory growth of the organism, i.e. approximately 18-45 degrees Celsius, and is conveniently carried out at a temperature of about 28 degrees Celsius. Ordinarily, optimum production is obtained after incubation periods of about 3-4 days. The fermentation may be carried out in flasks and in laboratory or industrial fermentors of various capacities. When tank fermentation is to be carried out, it is desirable to produce a vegetative inoculum in a nutrient broth by inoculating the broth culture with a slant or soil culture or a lyophilized culture of the organism. After obtaining an active inoculum in this manner, it is transferred aseptically to the fermentation tank medium for large scale production of the antibiotic. The medium in which the vegetative inoculum is produced can be the same as, or different from, that utilized in the tank for the production of the new antibiotic as long as it is such that a good growth of the microorganism is obtained.

Production of the BU-3285T antibiotic can be followed during the fermentation by testing samples of the broth or extracts of the mycelial solids for antibiotic activity against organisms known to be sensitive to the antibiotic. Assay organisms useful in testing this antibiotic are *Candida albicans* A9540 and *Cryptococcus neoformans* IAM4514. The bioassay is preferably performed by paper-disc assay on agar plates.

When fermentation is complete BU-3285T is recovered from the fermentation broth and separated from three known co-produced substances, pentalenolactone, aburamycin and chromomycins, by extraction with a suitable organic solvent followed by a series of column chromatographies. Examples 1 and 2 below illustrate specific procedures for obtaining BU-3285T in substantially purified form.

EXAMPLE 1

Fermentation of BU-3285T

A well grown agar slant of *Chainia rosea* Strain No. L827-7 was used to inoculate a 500 ml Erlenmeyer flask containing 100 ml of vegetative medium consisting of 2% malt extract (Oriental), 2% corn steep liquor (Oji Corn Starch Co.), 0.5% NaCl, 0.02% $K_2HPO_4$ and 0.2% $CaCO_3$ (pH 7.0, before sterilization).

The vegetative medium was incubated at 28° C. for 3 days on a rotary shaker (200 rpm) and 5 ml of the culture was then transferred into a 500 ml Erlenmeyer flask containing 100 ml of the production medium having the same composition as the vegetative medium. The fermentation was carried out at 28° C. for 4 days on a rotary shaker. The antibiotic production in the fermentation broth was determined by the paper-disc agar diffusion method using *Candida albicans* A9540 as the test organism.

The fermentation was also carried out in a tank fermentor. A two-liter portion of the seed culture prepared in the flask fermentation was inoculated into 120 liters of the production medium in a 200 liter tank fermentor. Fermentation was carried out at 28° C. with an agitation rate of 250 rpm and an aeration rate of 120 liters per minute. The antibiotic production reached a maximum of 30 μg/ml after a 70 hour fermentation.

EXAMPLE 2

Extraction and Purification

Harvested broth (58 L, pH 7.5), prepared according to the procedure given in Example 1, was added with n-butanol (40 L) and stirred for 1 hr. The mixture was separated into the organic and the aqueous layer with the aid of a Sharples centrifuge (Kokusan, No. 4A). The organic extract (30L) was concentrated in vacuo azeotropically by occasional addition of water to one liter. The concentrate was added dropwise into n-hexane (10 L) to precipitate the antibiotic complex (32.2 g) as a dark brown solid. The crude solid was dissolved in 50% aqueous methanol (300 ml) and applied on a column of Diaion HP-20 (Mitsubishi Kasei, φ 8×20 cm). After being washed with 50% aqueous methanol (2.8L), the column was developed with 80% aqueous methanol and then 80% aqueous acetone. The eluate was collected in 120 ml fractions which were examined by paper disc assay using *Cryptococcus neoformans* IAM4514 as the test strain. The active fractions were pooled and concentrated in vacuo to give a brown residue (11.0 g). The residue was chromatographed on a column of silica gel (Wako gel C-200, φ 4×70 cm) first using n-hexane-acetone (1:1 v/v) and then acetone as eluent. The eluates were monitored on the basis of bioassay (*C. neoformans* IAM4514) and TLC (SiO$_2$, n-butanol-acetic acid-water =4:1:1 v/v). After elution of the co-produced antibiotics with n-hexane-acetone (1:1 v/v), BU-3285T was eluted with acetone. The appropriate fractions were combined and concentrated in vacuo. The residue was chromatographed on a reversed phase silica gel column (ODS-60, 350/250 mesh, Yamamura Chemical Lab, column φ 4×32 cm) which had been pretreated with M/15 phosphate buffer (pH 7.0)-acetonitrile (8:2 v/v). After being washed with the same solvent (5 liters), the column was developed with M/15 phosphate buffer (pH 7.0)-acetonitrile (7:3 v/v) to elute BU-3285T. Concentration of the corresponding fractions followed by desalting on Diaion HP-20 afforded semi-pure solid (2.2 g). The solid was treated with EDTA (2 g) in 10% aqueous methanol (pH 9.0, 100 ml) and the solution was passed through a column of Diaion HP-20 (40 ml) for removal of the excess EDTA. The active solid recovered was chromatographed on a column of Sephadex LH-20 (φ 4×40 cm) using methanol as the developing solvent. Upon monitoring the eluate using the bioassay (*C. neoformans* IAM4514) and TLC described above, the appropriate fractions were concentrated in vacuo to yield 753 mg of pure BU-3285T as a white amorphous powder.

Physico-chemical Properties

Figure 2:
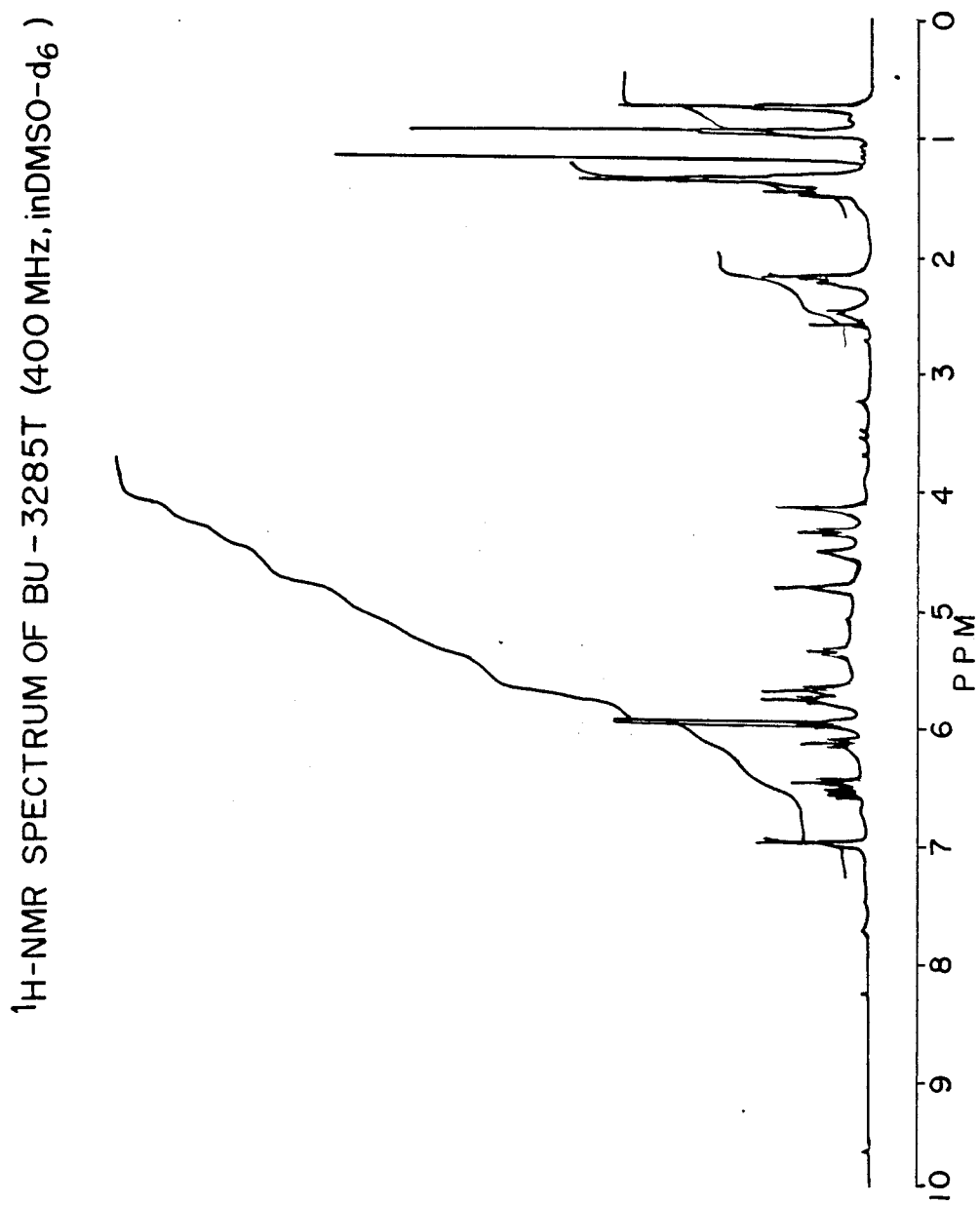
FIG. 2 shows the $^1$H-NMR spectrum of BU-3285T (400 MHz, in DMSO-$d_6$).

BU-3285T was obtained as a white amorphous solid. This solid was soluble in water, methanol, ethanol and dimethyl sulfoxide, slightly soluble in acetone and ethyl acetate but insoluble in chloroform and n-hexane. It gave positive response to iodine vapor and sulfuric acid, but negative response to ninhydrin and anthrone tests. The FAB-mass spectrum of BU-3285T showed pseudomolecular ions at m/z 493 (M+H)$^+$, 515 (M+Na)$^+$ and 531 (M+K)$^+$ which corresponded to a molecular weight of 492. The molecular formula of BU-3285T was established as $C_{23}H_{33}O_8SNa$ by high resolution FAB-mass spectrum [M+Na$^+$, m/z 515.1692; calcd. for $C_{23}H_{33}O_8SNa_2$, m/z 515.1714]. The physico-chemical properties of BU-3285T are summarized in Table 3. The IR spectrum (FIG. 1) showed absorption bands at 3400, 2930, 1720, 1635, 1460 and 1260 cm$^{-1}$. The strong carbonyl absorption at 1720 cm$^{-1}$ suggested an α, β-unsaturated δ-lactone, and the absorption at 1260 cm$^{-1}$ suggested a sulfate group in the antibiotic. The UV spectrum of BU-3285T had characteristic maxima at 260, 269 and 279 nm which did not change in acidic and alkaline solution, indicating a conjugated triene group in the molecule. The $^1$H-NMR spectrum of BU-3285T (Table 4 and FIG. 2) exhibited two methyl (δ: 0.64 and 0.87), five methylene (δ:1.23 - 1.29, 1.36, 2.10, and 2.17 & 2.38), five methine (δ:1.23 - 1.29, 4.09, 4.29, 4.46, and 4.79) and ten olefinic protons (δ:5.35, 5.67, 5.74, 5.79, 5.95, 6.00, 6.14, 6.47, 6.54 and 6.99). The $^{13}$C-NMR (Table 5) of BU-3285T showed 23 carbon signals including two methyl (δ:8.7 and 13.9), five methylene (δ:21 - 37), five methine (δ:40 - 82), ten sp$^2$ (δ:120 - 147) and one carbonyl carbon (δ:163.4).

Structural Determination

As previously noted, BU-3285T has been determined to have a molecular formula of $C_{23}H_{33}O_8SNa$ by high resolution FAB- mass spectrometry. The UV absorption maxima at 260, 269 and 279 nm suggest the presence of a triene group in the antibiotic. Its IR spectrum contained strong absorptions at 1720 and 1260 cm$^{-1}$ assignable to an α, β-unsaturated δ-lactone and an O-sulfo group, respectively. A fragment ion (M-SO$_3$Na$^-$, m/z 389 was observed together with the pseudomolecular ion (M-H—, m/z 491) in the negative SIMS spectrum, supporting the presence of a monosodium sulfate ester in BU-3285T. Among ten olefinic protons in the ¹H-NMR of BU-3285T, the signals at δ: 5.95 and 6.99 were assigned to the α- and β-proton, respectively, of the α, β-unsaturated δ-lactone. In the ¹H-¹H COSY experiment, this δ-proton was coupled to a methine proton bearing a hydroxyl (δ: 4.09) which in turn was coupled to another O-bearing methine proton (δ: 4.79) to form the δ-lactone ring. The COSY study further clarified that the proton at δ:4.79 connected to a trans double bond (δ: 5.69 and 5.79) and then to CH₂.CH(OSO₃Na).CH(CH₃)-CH(OH)- establishing the partial structure (A). The position of the sulfate was determined by the ¹³C-NMR, in which C-9 resonated at considerably lower field (δ:71.0). The positions of the hydroxyl groups were confirmed by ca.1 ppm lower field shift of the corresponding protons by acetylation. The remaining six olefinic protons (δ:5.35, 5.74, 6.00, 6.14, 6.47 and 6.54) were assigned as the conjugated triene moiety which had been deduced from the UV spectrum. The observed couplings indicated a cis, cis, trans trienoic structure (partial structure B). The ¹H- and ¹³C-NMR spectra clearly showed that the remaining part is a n-pentyl group (partial structure C, δ:21.9, 28.4, 30.8, 32.4 and 13.9).

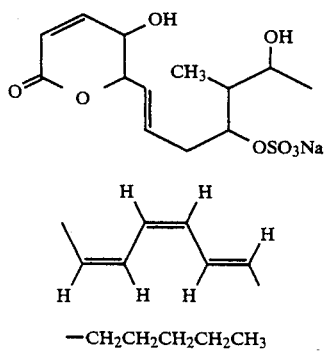

A

B

—CH₂CH₂CH₂CH₂CH₃          C

The long range ¹H-¹³C COSY study revealed the connectivity of the three partial structures establishing the total structure of BU-3285T as below.

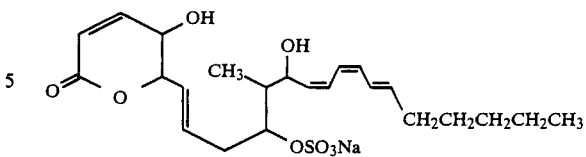

From the foregoing it has been determined that the novel antitumor antibiotic BU-3285T which is produced by *Chainia rosea* strain No. L 827-7 fermentation is an acidic hydrophilic compound showing characteristic triene absorption in the UV spectrum. The structural studies using two dimensional NMR experiments and mass spectrometry have identified that BU-3285T is a novel molecule possessing a pyrone ring, a conjugated triene and a monosodium sulfate moiety. The structure is partly related to those of fostriecin and its analogs. However, it is different from the known antibiotics in having a unique monosodium sulfate ester functionality.

BU-3285T exhibits in vitro antifungal activity and cytotoxicity, and potent in vivo inhibitory activity against P388 and L-1210 leukemia and B16 melanoma implanted in mice. The structurally related antibiotic fostriecin and its analogs were reported to have no antifungal activity and no antitumor effect against B16 melanoma. BU-3285T was also found to be a specific inhibitor of protein synthesis in L-1210 leukemia cells.

TABLE 3

| Physico-chemical Properties of BU-3285T | |
|---|---|
| Nature | White amorphous solid |
| M.P. (dec.) | 123–125° C. |
| $[\alpha]_D^{24}$ (c 1.0, MeOH) | +23° |
| UV $\lambda_{max}$ nm (ε) | 260(25,600), 269(31,600), 279(24,400) |
| Molecular formula | C₂₃H₃₃O₈SNa |
| FAB-mass (m/z) | 493(M + H)⁺, 515(M + Na)⁺, 531(M + K)⁺ |
| HR-FAB-mass | 515.1692 (M + Na)⁺ (Calcd for C₂₃H₃₃O₈SNa₂, m/z 515,1714) |
| TLC, SiO₂ (n-butanol-acetic acid-H₂O = 4:1:1 v/v) | Rf 0.42 |

TABLE 5

| ¹³C-NMR Spectrum of BU-3285T (100 MHz in DMSO-d₆) | | | |
|---|---|---|---|
| C-1 | 163.4 (s)* | C-13 | 123.0 (d) |
| 2 | 120.9 (d) | 14 | 123.5 (d) |
| 3 | 146.9 (d) | 15 | 129.7 (d) |
| 4 | 61.6 (d) | 16 | 125.6 (d) |
| 5 | 81.4 (d) | 17 | 136.5 (d) |
| 6 | 126.8 (d) | 18 | 32.4 (t) |
| 7 | 131.9 (d) | 19 | 28.4 (t) |
| 8 | 36.8 (t) | 20 | 30.8 (t) |
| 9 | 71.0 (d) | 21 | 21.9 (t) |
| 10 | 40.1 (d) | 22 | 13.9 (q) |
| 11 | 66.8 (d) | 23 | 8.7 (q) |
| 12 | 135.2 (d) | | |

*Multiplicity in off-resonance spectrum

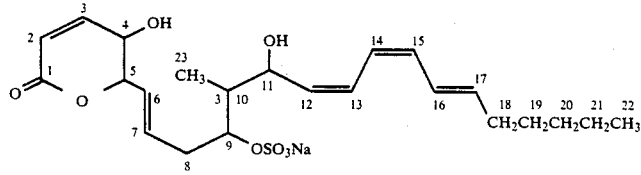

Antitumor Activity of BU-3285T

BU-3285T was tested for in vitro cytotoxicity against several murine and human tumor cell lines and for in vivo antitumor activity in mice. Mitomycin C was used as a reference compound in both in vitro and in vivo experiments. B16-F10 (murine melanoma) and Moser (human colorectal carcinoma) cells were grown to the logarithmic phase in an enriched Eagle minimum essential medium supplemented with fetal calf serum (FCS, 10%) and kanamycin (60 μg/ml); HCT-116 (human colon carcinoma) cells were in McCoy's 5A medium supplemented with FCS (10%), penicillin (100 U/ml) and streptomycin (100 μg/ml); and P388 (murine lymphocytic leukemia) cells and its vincristine-resistant subline (P388/VCR) were in RPMI 1640 medium supplemented with FCS (10%), penicillin (100 U/ml) and streptomycin (100 μg/ml).

B16-F10, Moser, HCT-116 and P388 cells were harvested and implanted into wells of a 96-well (for B16-F10, Moser and HCT-116 cells) or a 24-well (for P388 cells) tissue culture plate with test materials at the inoculum sizes of $3 \times 10^4$, $6 \times 10^4$, $6 \times 10^4$ and $2 \times 10^4$ cells/ml, respectively. They were incubated at 37° C. in a humidified atmosphere of 5% $CO_2$ and 95% air for 72 hrs. The cytotoxicity was colorimetrically determined at 540 nm after staining viable cells with 0.006% neutral red solution. For P388 cells, the number of viable cells was determined by a Coulter counter. As shown in Table 6, among three non-leukemia cell lines, B16-F10, HCT-116 and Moser cells, BU-3285T exhibited the most potent cytotoxic activity against Moser cells (naturally occurring drug-resistant cells). Interestingly, this compound showed almost the same cytotoxicity against P388/VCR as compared to that against its parent cells.

Inhibitory effects of BU-3285T on macromolecule biosynthesis (DNA, RNA and protein) were determined in cultured L1210 murine leukemia cells. The cells ($5 \times 10^5$ cells/ml) were incubated with the compound at 37° C. for 15 minutes and then further incubated for 60 minutes after the addition of labelled precursor, $^3$H-thymidine, $^{14}$C-uridine or $^3$H-leucine into the cultured mixture. After washing with chilled 5% trichloroacetic acid solution, the radioactivity incorporated into the acid-insoluble fraction of the cells was determined by a liquid scintillation counter. As shown in Table 7, BU-3285T inhibited protein synthesis 18 times stronger than RNA synthesis. This compound showed no significant inhibitory effect on DNA synthesis at 100 μg/ml, the highest concentration tested.

In vivo antitumor activity of BU-3285T was determined in experimental mouse tumor systems. Female $CDF_1$ mice were intraperitoneally inoculated with 0.4 ml of diluted ascitic fluid containing $10^6$ lymphocytic leukemia P388 cells or $10^5$ lymphoid leukemia L1210 cells and male $BDF_1$ mice were intraperitoneally inoculated with 0.5 ml of 10% melanotic melanoma B16 brei. Test compounds were intraperitoneally administered to the mice by the following treatment schedules; on days 1, 2 and 3 (Q1D×3) or on days 1, 4 and 7 (Q3D×3). As shown in Tables 8, 9 and 10, BU-3285T showed good antitumor activity in all tumor systems tested. When compared with mitomycin C, the activity of this compound was comparable against P388 leukemia but somewhat weaker against B16 melanoma and L1210 leukemia in terms of minimum effective dose.

TABLE 6

In vitro Cytotoxicity Against Murine and Human Tumor Cells

| Compound | IC$_{50}$ (μg/ml) | | | | |
|---|---|---|---|---|---|
| | B16-F10 | HCT-116 | Moser | P388 | P388/VCR |
| BU-3285T | 13.3 | 3.4 | 0.85 | 3.8 | 4.4 |
| Mitomycin C | 0.5 | 0.8 | 1.2 | ND* | ND |

*ND: Not done

TABLE 7

Inhibition of Macromolecule Biosynthesis in L1210 Leukemia Cells

| Compound | IC$_{50}$ (μg/ml) | | |
|---|---|---|---|
| | DNA | RNA | Protein |
| BU-3285T | >100 | 14.4 | 0.78 |
| Mitomycin C | 1.7 | >100 | >100 |

TABLE 8

Antitumor Activity of BU-3285T Against P388 Leukemia (ip)

| Compound | Dose (mg/kg/day) | Treatment schedule (ip) | MST*[1] (day) | T/C (%) | Body wt. change on day 4 (g) |
|---|---|---|---|---|---|
| BU-3285T | 10 | Q1D × 3 | 16.0 | 160*[2] | 0.0 |
| | 3 | " | 15.0 | 150*[2] | +1.5 |
| | 1 | " | 14.0 | 140*[2] | +1.0 |
| | 0.3 | " | 13.0 | 130*[2] | +1.0 |
| | 0.1 | " | 12.0 | 120 | +1.5 |
| Mitomycin C | 3 | Q1D × 3 | 20.0 | 200*[2] | −1.0 |
| | 1 | " | 13.5 | 135*[2] | +0.5 |
| | 0.3 | " | 14.0 | 140*[2] | +1.0 |
| | 0.1 | " | 11.5 | 115 | +1.8 |
| Vehicle | — | Q1D × 3 | 10.0 | — | +1.3 |

*[1]Median survival time
*[2]Indicates significant antitumor effect (T/C ≧ 125%)

TABLE 9

Antitumor Activity of BU-3285T Against L1210 Leukemia (ip)

| Compound | Dose (mg/kg/day) | Treatment schedule (ip) | MST*[1] (day) | T/C (%) | Body wt. change on day 6 (g) |
|---|---|---|---|---|---|
| BU-3285T | 10 | Q1D × 3 | 10.5 | 150*[2] | 0.0 |
| | 3 | " | 9.0 | 129*[2] | +1.5 |
| | 1 | " | 9.0 | 129*[2] | +1.5 |
| | 0.3 | " | 8.0 | 114 | +2.5 |
| | 0.1 | " | 8.0 | 114 | +2.3 |
| Mitomycin C | 3 | Q1D × 3 | 13.0 | 186*[2] | −2.5 |
| | 1 | " | 9.5 | 136*[2] | +0.3 |
| | 0.3 | " | 10.0 | 143*[2] | +2.3 |
| | 0.1 | " | 8.5 | 121 | +2.5 |
| Vehicle | — | Q1D × 3 | 7.0 | — | +3.1 |

*[1]Median survival time
*[2]Indicates significant antitumor effect (T/C ≧ 125%)

TABLE 10

Antitumor Activity of BU-3285T Against B16 Melanoma (ip)

| Compound | Dose (mg/kg/day) | Treatment schedule (ip) | MST*[1] (day) | T/C (%) | Body wt. change on day 5 (g) |
|---|---|---|---|---|---|
| BU-3285T | 10 | Q3D × 3 | 21.5 | 126*[2] | +0.5 |
| | 3 | " | 26.5 | 156*[2] | 0.0 |
| | 1 | " | 22.5 | 132*[2] | +0.5 |
| | 0.3 | " | 20.0 | 118 | +0.3 |
| | 0.1 | " | 18.5 | 109 | +0.8 |
| Mitomycin C | 2 | Q3D × 3 | 34.5 | 203*[2] | 0.0 |
| | 1 | " | 23.0 | 135*[2] | +1.0 |
| | 0.5 | " | 22.0 | 129*[2] | +0.3 |
| | 0.25 | " | 20.0 | 118 | +0.3 |

TABLE 10-continued

Antitumor Activity of BU-3285T Against B16 Melanoma (ip)

| Compound | Dose (mg/kg/ day) | Treatment schedule (ip) | MST*[1] (day) | T/C (%) | Body wt. change on day 5 (g) |
|---|---|---|---|---|---|
| Vehicle | — | Q3D × 3 | 17.0 | — | +0.8 |

*[1]Median survival time
*[2]Indicates significant antitumor effect (T/C ≧ 125%)

In vitro antifungal activity of BU-3285T

In vitro antifungal activity was determined against various fungi by the serial agar dilution method. Sabouraud dextrose agar (pH 7.0) was used for the experiment. The inoculum size was adjusted to $10^6$ CFU/ml. After incubation at 28° C. for 40 hours, the minimum inhibitory concentration (MIC) was examined. As summarized below, BU-3285T showed relatively good and broad antifungal profile.

| Test organism | MIC (μg/ml) | | |
|---|---|---|---|
| | B.U.-3285T | Amphotericin B | Ketoconazole |
| Candida albicans IAM4888 | 25 | 1.6 | 50 |
| C. albicans A9540 | 25 | 1.6 | 50 |
| Cryptococcus neoformans D49 | 1.6 | 0.8 | 0.4 |
| C. neoformans IAM4514 | 1.6 | 0.8 | 0.4 |
| Aspergillus fumigatus IAM2530 | 25 | 3.1 | 3.1 |
| A. fumigatus IAM2034 | >100 | 3.1 | 6.3 |
| A. flavus FA21436 | 50 | 1.6 | 0.4 |
| Fusarium moniliforme A2284 | 25 | 3.1 | 6.3 |
| Piricularia oryzae D91 | 50 | 12.5 | 3.1 |
| Trichophyton mentagrophytes D155 | 25 | 6.3 | 1.6 |
| T. mentagrophytes #4329 | 12.5 | 6.3 | 1.6 |
| Blastomyces dermatidis D40 | 12.5 | 12.5 | 0.4 |
| Sporothrix schenckii IFO8158 | 100 | >100 | 6.3 |
| Petriellidium boydi IFO8078 | 0.8 | >100 | 1.6 |
| Mucor spinosus IFO5317 | 25 | 6.3 | 100 |

Subsequent to the filing of U.S. patent application Ser. No. 378,677, now abandoned on July 12, 1989, certain sulfatase enzymes were found to cleave the sulfate linkage of BU-3285T to produce desulfated BU-3285T having the formula

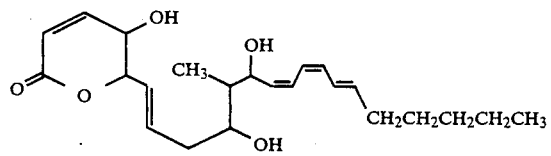

The desulfated derivative exhibited in vitro cytotoxicity similar to that of the parent antibiotic. The desulfated compound was not active in one in vivo test carried out in the murine lymphocytic leukemia P388 system. The desulfated compound exhibited no activity against fungi in vitro.

BU-3285T was treated with sulfatase enzymes obtained from various sources (Table 11; Sigma Chemical Co.) at pH 7.5 or pH 5.0. The products were analyzed by Silica gel TLC (Kiesel gel 60F$_{254}$) with detection by scanning at OD 254 nm (Shimadzu Co.). As described in Table 11, H-5 sulfatase (S-3009 type H-5) produced the desulfated derivative of BU-3285T in a good yield at both pH 7.5 and 5.0. The other three sulfatases listed in the table also produced the desulfate with much lower yield. Example 3 below illustrates preparation of desulfated BU-3285T.

TABLE 11

Sulfatase reaction of BU-3285T

| Sigma No. | Type | Source | pH* | Defulfated BU-3285T (%) |
|---|---|---|---|---|
| S-3009 | H-5 | Helix pomatia | 7.5 | 90 |
|  |  |  | 5.0 | 90 |
| S-8629 | V | Limpets (Petella vulgata) | 7.5 | 2 |
|  |  |  | 5.0 | 2 |
| S-1629 | VI | Aerobactor aerogenes | 7.5 | 3 |
| S-9629 | VII | Abalone Entrails | 7.5 | 5 |
|  |  |  | 5.0 | 5 |

| Reaction condition | |
|---|---|
| Substrate | (BU-3285T, 0.4 mg/50 μl-$H_2O$) |
| Each Enzyme | 5 units/100 μl-buffer |
| Each buffer | 200 μl |
| $H_2O$ | 150 μl |
| Total | 500 μl |
| Incubate at 37° C., 18 hrs. | |

*Buffer:
0.1M Tris-HCl, pH 7.5
0.2M Acetate, pH 5.0
Detection: The reaction mixture 20 μl was loaded on a Silica gel plate (Merck Co.) and the plate was developed with a solvent system of $CHCl_3$—MeOH (5:1, v/v). The TLC plate was scanned by reading OD 254 nm.

EXAMPLE 3

Preparation of BU-3285T Desulfate

A solution of BU-3285T (45 mg) and sulfatase (28 mg, S-3009 type H-5) in 0.1 M tris-HCl buffer (pH 7.5, 10 ml) was incubated at 37° C. for 18 hours. The reaction mixture was poured into water (40 ml) and then extracted with two 50 ml portions of ethyl acetate. The extracts were combined and evaporated to dryness in vacuo to afford a pale yellow residue (27 mg). The residue was purified by preparative TLC using a solvent system of methylene chloride:methanol (5:1 v/v) followed by column chromatography on Sephadex LH-20 (12 ×40 cm) using methanol as a developing solvent. Upon monitoring the eluate by TLC ($SiO_2$, methylene chloride:methanol, 5:1 v/v), the appropriate fractions were pooled and concentrated in vacuo to yield 8 mg of BU-3285T desulfate as a white amorphous powder.

Physico-chemical Properties of BU-3285T Desulfate

BU-32B5T desulfate was obtained as a white amorphous solid. This solid is soluble in methanol, ethanol, acetone and dimethyl sulfoxide, slightly soluble in water, but insoluble in carbon tetrachloride and n-hexane. It gave positive response to iodine vapor and sulfuric acid, but negative response to ninhydrin and anthrone tests. The positive FAB-mass spectrum of BU-3285T desulfate showed pseudomolecular ions at m/z 413 (M+Na)$^+$ and 429 (M+K)$^+$ which correspond to a molecular weight of 390. Its molecular formula was estimated to be $C_{23}H_{34}O_5$ by spectrometory analyses, suggesting that it was a desulfated derivative of BU-3285T. The physico-chemical properties of BU-3285T desulfate are summarized in Table 12. The IR spectrum showed absorption bands at 3410, 2930, 2850, 1715, 1670, 1635, 1450, 1380, 1085 and 1035 cm$^{-1}$. The strong absorption at 1260 cm$^{-1}$ assignable to a sulfate group is observed in the parent antibiotic but is missing in the product. The UV spectrum of BU-3285T desulfate has the absorption maxima at 260, 270 and 280 nm which did not change in acidic and alkaline solution as in the case of BU-3285T, showing the retention of a conjugated triene group in the molecule. Its $^1$H-NMR spectrum (Table 13) closely resembles that of BU-3285T, except that the methine proton attached to the carbon atom bearing a sulfate group in the latter moved to the up-field ($\delta$ 4.46 to $\delta$ 3.94) in the former. These spectral data indicated that the product retained all other structural features, but contained a hydroxyl group in place of the sulfate group of BU-3285T.

TABLE 12

Physico-chemical properties of BU-3285T desulfate

| | |
|---|---|
| Nature | White amorphous solid |
| M.P. (dec.) | 233–226° C. |
| UV $\lambda_{max}^{MeOH}$nm ($\epsilon$) | 260(25,300), 270(31,500), 280(24,600) |
| Molecular formula | $C_{23}H_{34}O_5$ |
| FAB-mass (m/z) | 413(M + Na)$^+$, 429(M + K)$^+$ |
| TLC, SiO$_2$ | |
| n-Butanol-acetic acid-H$_2$O = 4:1:1 v/v | Rf 0.70 |
| CH$_2$Cl$_2$—MeOH = 5:1 v/v | Rf 0.62 |

TABLE 13

$^1$H-NMR spectra of BU-3285T and its desulfate derivative (400 MHz in DMSO-d$_6$)

| Proton | BU-3285T | BU-3285T desulfate |
|---|---|---|
| 23-CH$_3$ | 0.64 (3H, d, J = 6.8 Hz) | 0.67 (3H, d, J = 6.8 Hz) |
| 22-CH$_3$ | 0.87 (3H, t, J = 6.8 Hz) | 0.86 (3H, t, J = 6.5 Hz) |
| 10-CH, 20-CH$_2$, 21-CH$_2$ | 1.23–1.29 (5H, m) | 1.23–1.26 (5H, m) |
| 19-CH$_2$ | 1.36 (2H, m) | 1.36 (2H, m) |
| 18-CH$_2$ | 2.10 (2H, m) | 2.11 (2H, m) |
| 8-CH$_2$ | 2.17 & 2.38 (2H, m) | 2.11 & 2.20 (2H, m) |
| 4-H | 4.09 (1H, dd, J = 5.4 & 2.9 Hz) | 4.05 (1H, m) |
| 11-H | 4.29 (1H, t, J = 10.2 Hz) | 4.33 (1H, m) |
| 9-H | 4.46 (1H, m) | 3.94 (1H, m) |
| 5-H | 4.79 (1H, dd, J = 7.3 & 2.9 Hz) | 4.81 (1H, dd, J = 7.7 & 2.5 Hz) |
| 12-H | 5.35 (1H, dd, J = 10.2 & 11.3 Hz) | 5.38 (1H, m) |
| 6-H | 5.67 (1H, dd, J = 15.7 & 7.3 Hz) | 5.67 (1H, m) |
| 17-H | 5.74 (1H, m, J = 15.1 & 7.3 Hz) | 5.71 (1H, m) |
| 7-H | 5.79 (1H, m) | 5.84 (1H, m) |
| 2-H | 5.95 (1H, d, J = 9.7 Hz) | 5.98 (1H, d, J = 9.8 Hz) |
| 15-H | 6.00 (1H, t, J = 11.3 Hz) | 6 (1H, m) |
| 13-H | 6.14 (1H, t, J = 11.3 Hz) | 6.15 (1H, t, J = 11.1 Hz) |
| 14-H | 6.47 (1H, t, J = 11.3 Hz) | 6.48 (1H, t, J = 11.1 Hz) |
| 16-H | 6.54 (1H, dd, J = 15.1 & 11.3 Hz) | 6.52 (1H, dd, J = 15.2 & 11.1 Hz) |
| 3-H | 6.99 (1H, dd, J = 9.7 & 5.4 Hz) | 7.01 (1H, dd, J = 9.8 & 5.5 Hz) |

Antitumor Activity of BU-3285T Desulfate

BU-3285T and its desulfated derivative, BU-3285T desulfate, were comparatively tested for in vitro cytotoxicity against murine and human tumor cell lines.

B16-F10 (murine melanoma), HCT-116 (human colon carcinoma), A549 (human lung carcinoma) and A549/VP29 (an etoposide-resistant subline of A549) were grown in Eagle's MEM (Nissui) supplemented with FCS (fetal calf serum, 10%) and non-essential amino acids (B16-F10), or in McCoy's 5A medium (Gibco) with FCS (10%), essential and non-essential amino acids, vitamins and antibiotics (HCT-116 and both of A549) at 37° C. under a humidified atmosphere in a 5% CO$_2$ incubator. Exponentially growing B16-F10, HCT-116 and A549 cells were harvested, counted and suspended in the culture medium at $1.5 \times 10^4$, $3 \times 10^4$ and $3 \times 10^4$ cells/ml, respectively. After planting 180 $\mu$l of cell suspension into wells of a 96-well microtiter plate on day 0, the test materials (20 $\mu$l) were added on day 1 and the plates were incubated for 72 hours. The cytotoxic activity was colorimetrically determined at 540 nm after staining viable cells with neutral red solution. The results are summarized in Table 14. Both BU-3285T and BU-3285T desulfate were quite active against the murine and human tumor cell lines and their IC$_{50}$ values were 1.9 - 38 $\mu$g/ml and 5.5 - 14 $\mu$g/ml, respectively. Interestingly, the desulfate gave almost the same cytotoxicity against the resistant tumor cell line A549/VP29 as compared to that against the parent cell line.

TABLE 14

In vitro cytotoxicity against murine and human tumor cells

| | IC$_{50}$ ($\mu$g/ml) | | | |
|---|---|---|---|---|
| Compound | B16-F10 | HCT-116 | A549 | A549/VP29 |
| Bu-3285T A | 38 | 1.9 | 4.1 | 17 |
| BU-3285T desulfate | 14 | 5.5 | 13 | 15 |
| Adriamycin | 0.03 | 0.30 | ND* | ND |
| VP16 | 0.21 | 5.3 | 1.2 | 40 |

*ND: Not done

Inhibitory effects of the above compounds on macromolecule (DNA, RNA and protein) biosynthesis were determined in cultured L1210 murine leukemia cells. The cells ($5 \times 10^5$ cells/ml) were incubated with the test materials at 37° C. for 15 minutes and then further incubated for 60 minutes after the addition of labeled precursor, $^3$H-thymidine, $^{14}$C-uridine or $^3$H-leucine into the cultured mixture. After washing with chilled 5% trichloroacetic acid solution, the radioactivity incorporated into the acid-insoluble fraction of the cells was determined with a liquid scintillation counter. As shown in Table 15, BU-3285T and BU-3285T desulfate potently inhibited RNA and protein synthesis with the IC$_{50}$ values of 5.8 and 2.4 $\mu$g/ml and 6.1 and 8.1 $\mu$g/ml, respectively. Both BU-3285T desulfate and the parent compound showed no significant inhibitory effect on DNA synthesis at 100 $\mu$g/ml, the highest concentration tested.

TABLE 15

Inhibition of macromolecule biosynthesis in L1210 leukemia cells

| | IC$_{50}$ ($\mu$g/ml) | | |
|---|---|---|---|
| Compound | DNA | RNA | Protein |
| BU-3285T A | >100 | 5.8 | 2.4 |
| BU-3285T desulfate | >100 | 6.1 | 8.1 |

As indicated above BU-3285T possesses inhibitory activity against fungal organisms and mammalian malignant tumors. BU-3285T desulfate demonstates inhibitory activity against mammalian tumors.

According to one aspect of the invention, therefore, there is provided a method for therapeutically treating an animal host affected by a fungal infection which comprises administering to said host an effective antifungal dose of BU-3285T.

In another aspect there is provided a method for therapeutically treating a mammalian host affected by a malignant tumor sensitive to BU-3285T or BU-3285T desulfate which comprises administering to said host an effective tumor-inhibiting dose of BU-3285T or BU-3285T desulfate, or a pharmaceutical composition containing BU-3285T or BU-3285T desulfate.

In yet another aspect of this invention a pharmaceutical composition is provided which comprises an effective antifungal amount of BU-3285T in combination with an inert pharmaceutically acceptable carrier or diluent. These compositions can be made up in any pharmaceutical form appropriate for parenteral administration.

In still another aspect a pharmaceutical composition is provided which comprises an effective tumor-inhibiting amount of BU-3285T or BU-3285T desulfate in combination with an inert pharmaceutically acceptable carrier or diluent. Those compositions can be made up in any pharmaceutical form appropriate for parenteral administration.

Preparations according to the invention for parenteral administration include sterile aqueous or non-aqueous solutions, suspensions or emulsions. They may also be manufactured in the form of sterile solid compositions which can be dissolved in sterile water, physiological saline or some other sterile injectable medium immediately before use.

It will be appreciated that the actual preferred dosages of the compounds of the present invention will vary according to the particular compound being used, the particular composition formulated, the mode of administration and the particular situs, host and disease being treated. Many factors that modify the action of the drug will be taken into account by those skilled in the art, e.g. age, body weight, sex, diet, time of administration, route of administration, rate of excretion, condition of the host, drug combinations, reaction sensitivities and severity of the disease. Optimal dosages for a given set of conditions can be ascertained by those skilled in the art using conventional dosage determination tests in view of the experimental animal data provided.

While the invention has been described with respect to various specific examples and embodiments, it is to be understood that the invention is not limited thereto.

What is claimed is:

1. The compound designated BU-3285T having the structural formula

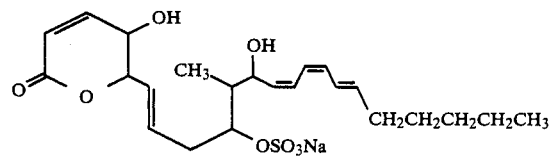

2. The compound designated BU-3285T desulfate having the formula

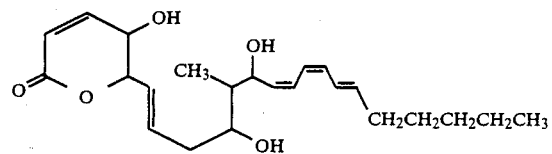

* * * * *